US012661044B2

(12) United States Patent
Hendriks et al.

(10) Patent No.: US 12,661,044 B2
(45) Date of Patent: Jun. 23, 2026

(54) PRESCRIBING A CPAP MASK BASED ON PATIENTS STRESS RESPONSE

(71) Applicant: KONINKLIJKE PHILIPS N.V., Eindhoven (NL)

(72) Inventors: Cornelis Petrus Hendriks, Eindhoven (NL); Joyce Van Zanten, Waalre (NL); Pedro Miguel Ferreira Dos Santos Da Fonseca, Antwerp (BE); Joachim Johannes Kahlert, Aachen (DE); Daan Anton Van Den Ende, Breda (NL); Jonathan Sayer Grashow, Pittsburg, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 171 days.

(21) Appl. No.: 18/371,796

(22) Filed: Sep. 22, 2023

(65) Prior Publication Data

US 2024/0099621 A1     Mar. 28, 2024

Related U.S. Application Data

(60) Provisional application No. 63/410,350, filed on Sep. 27, 2022.

(51) Int. Cl.
*A61B 5/00* (2006.01)
*A61B 5/0205* (2006.01)
*A61B 5/16* (2006.01)
*G16H 20/30* (2018.01)

(52) U.S. Cl.
CPC ............ *A61B 5/165* (2013.01); *A61B 5/0205* (2013.01); *A61B 5/4884* (2013.01); *A61B 5/6803* (2013.01); *G16H 20/30* (2018.01);

*A61B 5/742* (2013.01); *A61B 2560/0443* (2013.01); *A61B 2562/0219* (2013.01)

(58) Field of Classification Search
None
See application file for complete search history.

(56) References Cited

U.S. PATENT DOCUMENTS

| | | |
|---|---|---|
| 9,168,344 B2 | 10/2015 | Rapoport |
| 9,597,029 B2 | 3/2017 | Patangay |
| 2012/0232240 A1 | 9/2012 | Smith |
| 2017/0186122 A1 | 6/2017 | Levings |
| 2018/0078212 A1 | 3/2018 | Brumfield |
| 2021/0319856 A1 | 10/2021 | Duckworth |
| 2022/0061752 A1 | 3/2022 | Heneghan |
| 2022/0076822 A1 | 3/2022 | Liu |

(Continued)

OTHER PUBLICATIONS

Edmonds J.C. et al., "Claustrophobic Tendencies and Continuous Positive Airway Pressure Therapy Non-adherence in Adults with Obstructive Sleep Apnea", Heart & Lung, 2015; 44(2): 100-106.

(Continued)

*Primary Examiner* — Lynsey C Eiseman
(74) *Attorney, Agent, or Firm* — Michael W. Haas

(57) ABSTRACT

Methods and systems for recommending at least one patient interface device from among a plurality of patient interface devices for a patient. The methods and systems monitor an initial stress response of the patient upon being exposed to each of the potential patient interface devices of the plurality and from such monitoring select a device or devices that produce lesser stress responses.

8 Claims, 2 Drawing Sheets

(56) References Cited

U.S. PATENT DOCUMENTS

| | | | |
|---|---|---|---|
| 2022/0226145 A1* | 7/2022 | Hao | A61M 16/0495 |
| 2023/0215290 A1* | 7/2023 | Shelly | G16H 20/40 |

OTHER PUBLICATIONS

Kappeler-Setz C. et al., "Towards Long Term Monitoring of Electrodermal Activity in Daily Life", Personal and Ubiquitous Computing, vol. 17 Issue 2, pp. 261-271, 2013.

Jindrova M. et al., "Skin Conductance Rise Time and Amplitude Discern Between Different Degrees of Emotional Arousal Induced by Affective Pictures Presented on a Computer Screen", 2020, pre-print https://www.biorxiv.org/content/10.1101/2020.05.12.090829v1.

Christopoulos G.I., "The Body and the Brain: Measuring Skin Conductance Responses to Understand the Emotional Experience", Organizational Research Methods, vol. 22, issue 1, pp. 394-420, 2019.

Xia L. et al., "A Physiological Signal-Based Method for Early Mental-Stress Detection", Biomedical Signal Processing and Control, vol. 46, pp. 18-32, 2018.

Baumgartl H. et al., "Two-Level Classification of Chronic Stress Using Machine Learning on Resting-State EEG Recordings", Americas Conference on Information Systems (AMCIS), Aug. 12-16, 2020.

* cited by examiner

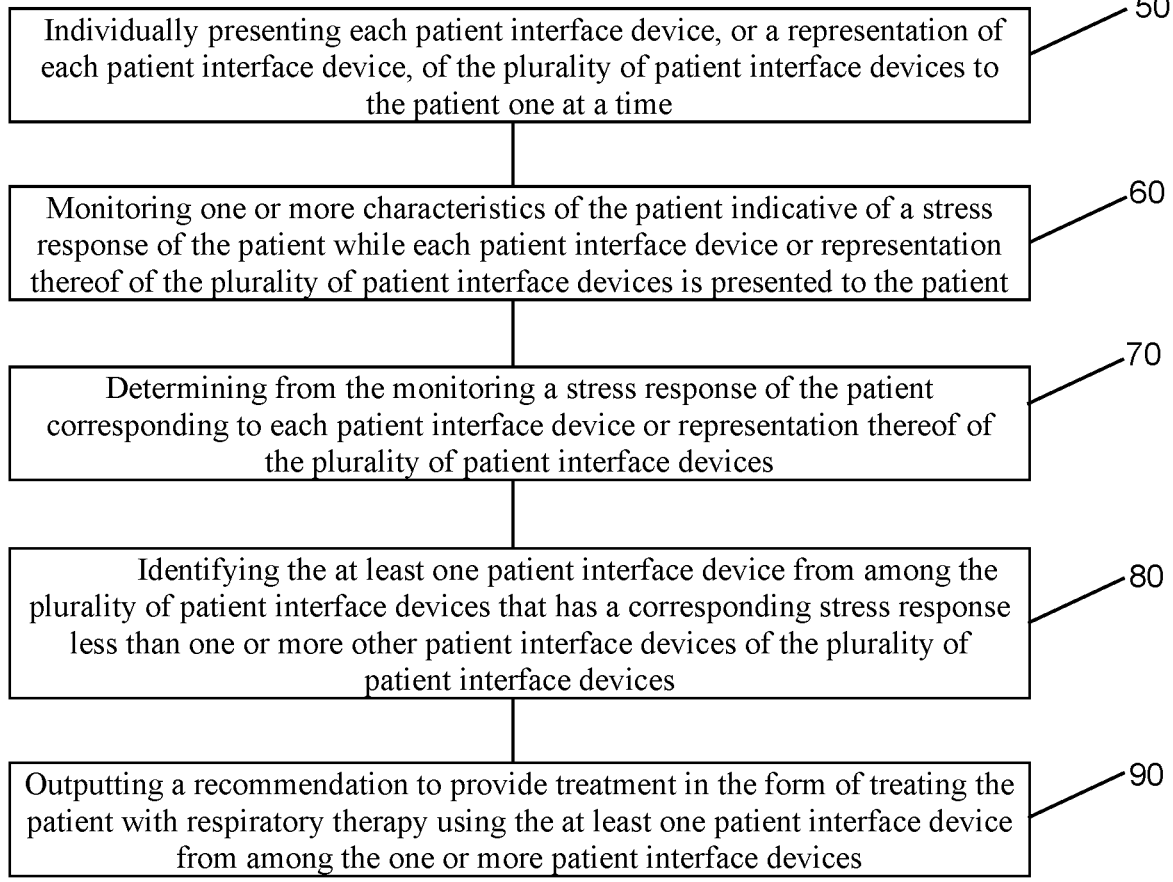

Individually presenting each patient interface device, or a representation of each patient interface device, of the plurality of patient interface devices to the patient one at a time ⟋50

Monitoring one or more characteristics of the patient indicative of a stress response of the patient while each patient interface device or representation thereof of the plurality of patient interface devices is presented to the patient ⟋60

Determining from the monitoring a stress response of the patient corresponding to each patient interface device or representation thereof of the plurality of patient interface devices ⟋70

Identifying the at least one patient interface device from among the plurality of patient interface devices that has a corresponding stress response less than one or more other patient interface devices of the plurality of patient interface devices ⟋80

Outputting a recommendation to provide treatment in the form of treating the patient with respiratory therapy using the at least one patient interface device from among the one or more patient interface devices ⟋90

FIG. 2

PRESCRIBING A CPAP MASK BASED ON PATIENTS STRESS RESPONSE

CROSS-REFERENCE TO RELATED APPLICATIONS

This patent application claims the priority benefit under 35 U.S.C. § 119(e) of U.S. Provisional Application No. 63/410,350, filed on Sep. 27, 2022, the contents of which are herein incorporated by reference.

BACKGROUND OF THE INVENTION

1. Field of the Invention

The present invention relates to systems and methods for treating conditions, such as sleep disordered breathing, using positive airway pressure (PAP) therapy, and more particularly, to systems and methods for identifying desirable medical devices that are particularly suited for a given patient.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component typically having a soft, flexible sealing cushion that engages the face of a patient. The mask component may be, without limitation, a nasal mask that covers the patient's nose, a nasal cradle that interfaces under a patient's nose, a nasal pillows mask that interfaces with the individual nostrils of a patient, a nasal/oral mask that covers the patient's nose and mouth, or a full face mask that covers the patient's face. Such patient interface devices may also employ other patient contacting components, such as forehead supports, cheek pads, chin pads, silicone frames, and headgear elements. The patient interface device is connected to a gas delivery tube or conduit and interfaces the pressure support device with the airway of the patient, so that a flow of breathing gas can be delivered from the pressure/flow generating device to the airway of the patient.

No two patients are exactly alike. As such, numerous different patient interface devices having numerous different features such as various shapes, materials, configurations, and the like exist and are selectable for a patient based upon fit and other appropriate criteria. Due to the wide variety of features in the various masks and the inability to know all of the characteristics of the patient that are relevant to the selection of a patient interface device, difficulty has been experienced in identifying the most appropriate patient interface device for a given patient based upon all of the various patient characteristics. Further, as remote diagnostic arrangements become more prevalent, as will arrangements which can provide for improved mask determinations without requiring human (e.g., practitioner) input.

SUMMARY OF THE INVENTION

Embodiments of the present invention provide a method of recommending at least one patient interface device from among a plurality of patient interface devices as being suited to provide treatment in the form of respiratory therapy to a patient. The method comprises: individually presenting each patient interface device, or a representation of each patient interface device, of the plurality of patient interface devices to the patient one at a time; monitoring one or more characteristics of the patient indicative of a stress response of the patient while each patient interface device or representation thereof of the plurality of patient interface devices is presented to the patient; determining from the monitoring a stress response of the patient corresponding to each patient interface device or representation thereof of the plurality of patient interface devices; identifying the at least one patient interface device from among the plurality of patient interface devices that has a corresponding stress response less than one or more other patient interface devices of the plurality of patient interface devices; and outputting a recommendation to provide treatment in the form of treating the patient with respiratory therapy using the at least one patient interface device from among the one or more patient interface devices.

Individually presenting each patient interface device, or a representation of each patient interface device, of the plurality of patient interface devices to the patient one at a time may comprise providing an actual sample of each patient interface device to the patient.

Individually presenting each patient interface device, or a representation of each patient interface device, of the plurality of patient interface devices to the patient one at a time may comprise providing an image of each patient interface device to the patient. Providing a number of images of each patient interface device to the patient may comprise providing a digital image of each patient interface device to the patient via a display.

Monitoring one or more characteristics of the patient indicative of a stress response of the patient while each patient interface device or representation thereof of the plurality of patient interface devices is presented to the patient may comprise monitoring one or more of: heart rate variability (HRV), blood pressure, the breathing pattern, the galvanic skin response (GSR), brain waves (EEG), limb/head/body movements, or facial expressions. Monitoring one or more characteristics of the patient indicative of a stress response of the patient while each patient interface device or representation thereof of the plurality of patient interface devices is presented to the patient may be carried out using one or more of: an optical sensor, an accelerometer, a bioimpedance sensor, a flow sensor, a $CO_2$ sensor. Individually presenting each patient interface device, or a representation of each patient interface device, of the plurality of patient interface devices to the patient one at a time may comprise individually presenting physical samples of each patient interface of the plurality of patient interface devices to the patient; and monitoring the one or more characteristics of the patient indicative of a stress response of the patient may comprise using one or more sensors integrated into each physical sample.

Outputting a recommendation to provide treatment in the form of treating the patient with respiratory therapy using the at least one patient interface device from among the one or more patient interface devices may comprise providing the at least one patient interface device to the patient.

As another aspect of the present invention, a machine structured to recommend at least one patient interface device from among a plurality of patient interface devices as being desirable to provide treatment in the form of respiratory therapy to a patient is provided. The machine comprises: a processor apparatus comprising a processor and a memory; an input apparatus structured to provide input signals to the processor apparatus; and an output apparatus structured to receive output signals from the processor apparatus, wherein the memory has stored therein instructions which, when executed on the processor, cause the machine to perform operations comprising: individually presenting to the patient one at a time, via the output apparatus, a number of images of each patient interface device of the plurality of patient interface devices; monitoring, via one or more sensors in communication with the input apparatus, one or more characteristics of the patient indicative of a stress response of the patient while each patient interface device or representation thereof of the plurality of patient interface devices is presented to the patient; determining from the monitoring a stress response of the patient corresponding to each patient interface device or representation thereof of the plurality of patient interface devices; identifying the at least one patient interface device from among the plurality of patient interface devices that has a corresponding stress response less than one or more other patient interface devices of the plurality of patient interface devices; and outputting, via the output apparatus, a recommendation to provide treatment in the form of treating the patient with respiratory therapy using the at least one patient interface device from among the one or more patient interface devices.

As yet a further aspect of the present invention, a non-transitory machine-readable storage medium having stored thereon instructions which, when executed on a processor apparatus of a machine that is structured to recommend at least one patient interface device from among a plurality of patient interface devices as being desirable to provide respiratory therapy to a patient is provided. The instructions cause the machine to perform operations comprising: individually presenting to the patient one at a time, via the output apparatus, a number of images of each patient interface device of the plurality of patient interface devices; monitoring, via one or more sensors in communication with the input apparatus, one or more characteristics of the patient indicative of a stress response of the patient while each patient interface device or representation thereof of the plurality of patient interface devices is presented to the patient; determining from the monitoring the stress response of the patient corresponding to each patient interface device or representation thereof; identifying the particular or more patient interface devices from among the plurality of patient interface devices that have corresponding stress levels less than one or more other patient interface devices of the plurality of patient interface devices; and outputting, via the output apparatus, a recommendation to provide treatment in the form of treating the patient with respiratory therapy using the at least one patient interface device from among the one or more patient interface devices.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 2 is a flowchart depicting certain aspects of an improved method in accordance with an example embodiment the present invention.

DETAILED DESCRIPTION OF EXEMPLARY EMBODIMENTS

Figure 1:
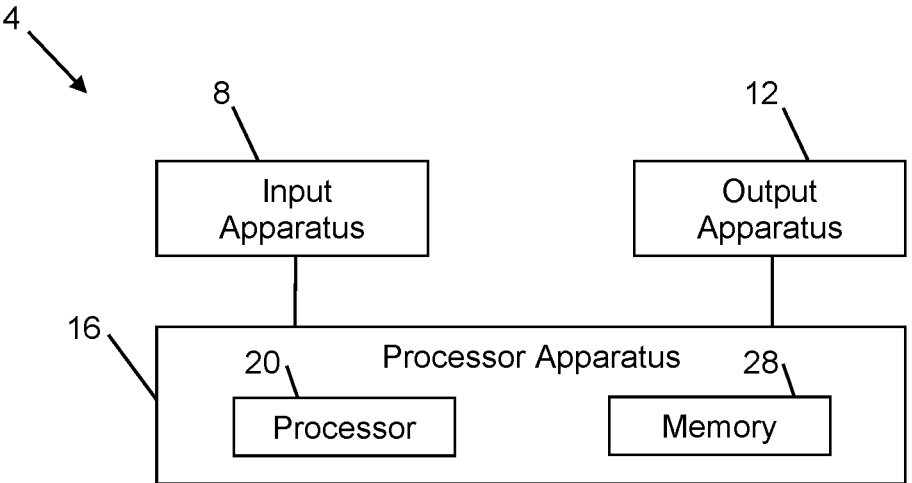
FIG. 1 is schematic depiction of an improved system in accordance with an example embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As discussed in the Background, there are a wide variety of features present in the various patient interface devices available today for providing PAP therapies and difficulty has been experienced in identifying the most appropriate patient interface device for a given patient based upon all of the various patient characteristics. Embodiments of the present invention improve upon conventional arrangements for identifying/selecting patient interface devices for a given patient by monitoring stress response of the patient during initial interaction(s) at the very beginning of a fitting process so as to identify, and thus avoid, potential device triggered anxiety disorders before they have the opportunity to develop, as anxiety disorders such as claustrophobia can lead to therapy non-adherence. Once anxiety has been induced it is difficult to turn around, hence avoiding such pathway in a patient's treatment regimen altogether provides a benefit not present in existing approaches.

A system 4 in accordance with one example embodiment of the present invention is depicted generally in FIG. 1. System 4 can be said to be operable to provide, from among a plurality of medical devices, a recommendation of a particular medical device or a small number of medical devices that are especially suited to a patient based at least in-part upon the stress response of a patient upon initial exposure of the patient to such devices or representations thereof. In the depicted examples presented herein, the medical device that is recommended by system 4 is in the exemplary form of a patient interface device that is configured to provide respiratory therapy to a patient, such as a CPAP mask or other type of patient interface device. It is understood, however, that the teachings herein are not intended to be limited to such patient interface devices and rather are applicable to other types of medical devices and other devices that are selected for use with a patient or other individual.

Continuing to refer to FIG. 1, system 4 includes an input apparatus 8, an output apparatus 12, and a processor apparatus 16. Input apparatus 8 is in communication with processor apparatus 16 and can be any of a wide variety of input devices that might include, for example and without limitation, keyboards (physical and/or touchscreen), CD ROM readers, electronic data interfaces that follow any of a variety of known protocols such as Small Computer Systems Interface (SCSI), IEEE 802.11, Ethernet, and the like, as well as other input devices, all of which are configured to provide input signals to processor apparatus 16. Output apparatus 12 is in communication with processor apparatus 16 and can be any of a wide variety of devices and may include, for example, video displays, printers, data interfaces such as those set forth in the preceding sentence, and other output devices that all receive output signals from processor apparatus 16.

In the example embodiment shown in FIG. 1, processor apparatus 16 includes a processor 20 and a memory 24 that are in communication with one another. Processor 20 may be, for example and without limitation, a microprocessor, a microcontroller, or some other suitable processing device or circuitry, that interfaces with memory 24. Memory 24 can be any of one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. Memory 24 has stored therein a set of instructions that are generally in the form of routines or other types of instructions which, when executed on/by processor 20, cause system 4 to perform certain predetermined functions. Other variations will be apparent to one of ordinary skill in the art.

Having thus described a basic example arrangement of system 4, certain operations of system 4 will now be described below in conjunction with an exemplary flowchart that is depicted generally in FIG. 2. As generally shown at 50, as an initial step each potential patient interface device that is being considered for use in treating the patient, or a representation of each patient interface device, is presented to the patient one at a time. Such presentation may be carried out in several ways without varying from the scope of the present invention. For example, an actual sample of each patient interface device (i.e., a working device or imitation thereof) may be presented to the patient. As another example, a number of images of each patient interface device may be presented to the patient. Such images may be provided in physical form to the patient or in digital form provided to the patient via a suitable electronic display provided, for example, without limitation, as output apparatus 12.

As each of the potential patient interface devices or representations thereof are being presented individually to the patient at 50, one or more characteristics of the patient that are indicative of a stress response of the patient are monitored, such as generally shown at 60. Such characteristics of the patient may include one or more of: heart rate variability (HRV), blood pressure, breathing pattern, galvanic skin response (GSR), brain waves (EEG), limb/head/body movements, or facial expressions. Such characteristics may be monitored, for example, without limitation, using one or more sensors of the type optical (PPG, camera), accelerometer, bioimpedance, flow, chemical ($CO_2$ indicating hyperventilation) or electrical (electrodes), and these sensors can be integrated into each of the sample patient interface devices provided to the patient, in a wearable device (e.g., a smartwatch and/or dedicated sensing arrangement), or a camera (e.g., without limitation, a webcam provided as part of a laptop, a front facing camera of a smartphone or electronic tablet, or other suitable arrangement). Input from such sensors can be received via input apparatus 8.

From the monitoring described at 60, a stress response of the patient corresponding to the patient's exposure to each patient interface device or representation thereof is determined, such as shown at 70. Patient interface devices which produce a greater stress response are more likely to be problematic in regard to creating anxiety, while those that produce a lesser stress response a more likely to not create anxiety and thus are preferred.

Next, as shown at 80, the at least one patient interface device from among the plurality of patient interface devices that has a corresponding stress response less than one or more other patient interface devices of the plurality of patient interface devices is identified by comparing the stress response corresponding to the exposure to each patient interface device or representation thereof.

Finally, as shown at 90, a recommendation to provide treatment in the form of treating the patient with respiratory therapy using the at least one patient interface device from among the one or more patient interface devices is output to the patient. Such output may be provided via output apparatus 12.

Having thus provided a general overview of system 4 and operation thereof some detailed example arrangements utilizing such system 4 and related concepts will now be described. In one example embodiment, system 4 is integrated in an arrangement such as the Philips Mask Selector 3D tool. Utilizing a remote PPG in the camera system thereof stress responses of a patient are determined for each patient interface device of a plurality of candidate devices otherwise determined by the Mask Selector tool. The anxiety risk classification is taken into consideration in the final mask recommendation. For example, by weighing mask options provided by the virtual fit algorithm of the Mask Selector tool: if two mask types have approximately the same fit, the mask type which caused the lowest stress response is recommended.

As another example, a stress response of the patient can be measured with different principles, for example by looking at the heart rate variability (HRV), blood pressure, the breathing pattern, the galvanic skin response (GSR), brain waves (EEG), limb/head/body movements, or facial expressions. Sensors can be of the type optical (PPG, camera), accelerometer, bioimpedance, flow, chemical ($CO_2$ indicating hyperventilation) or electrical (electrodes), and these sensors can be integrated in the mask, the device, a skin-contacting wearable, or a camera. Stress signals can be acquired during the following events and situations:

Baseline (home, sleep lab). Preferably, a baseline stress signal of the patient is acquired when the patient is in a relatively comfortable state, for example awake or asleep without obstructions, or in a sleep lab during the OSA diagnosis. This includes environmental effects.

During the titration night (sleep lab, home). The patient sleeps with the mask in the sleep lab or at home while the positive airway pressure is adjusted to find the right settings for the patient. This potentially triggers a stress response due to claustrophobia, EPI and arousals due to (residual) obstructions.

Before mask strap on (DME). The therapist looks at the patient's facial anatomy (shape and size) and asks if the patient is a mouth or nose breather. The therapist shows pictures or demos of mask types to the patient and asks for the patient's preferences. This potentially triggers a stress response due to the perception of claustrophobia, or a general preference/anxiety towards a certain mask design. Option: pressure sensors between the skin and the mask quantify the stimulation of tactile sensors.

During mask strap on (DME). Based on the information from the previous step a mask is selected and strapped to the head to check the basis fit. This potentially triggers a stress response due to claustrophobia and tactile receptor hypersensitivity.

During device instruction and pressure supply (DME). During further instruction the PAP device is explained, and a positive pressure is applied for demonstration and practicing purposes. This potentially triggers a stress response caused due to expiratory pressure intolerance (EPI). Optimize C-flex, A-flex, BiPAP settings accordingly.

During the above procedures stress signals are acquired and event data are logged (e.g., with a selection button in a web-app, or retrieved from an agenda or planner). Time-stamped signals and data are streamed to a storage and processing unit (device, computer, cloud etc.). As a result of the perceived stress levels per mask type, a recommendation can be made to start therapy with the best scoring mask with respect to stress instead of the optimal mask for therapy. Such approach provides for the patient to get familiar to the therapy with the least amount of stress. The patient can then gradually work towards the most optimal mask for both stress and therapy.

It is contemplated that aspects of the disclosed concept can be embodied as computer readable codes on a tangible computer readable recording medium. The computer readable recording medium is any data storage device that can store data which can be thereafter read by a computer system. Examples of the computer readable recording medium include read-only memory (ROM), random-access memory (RAM), CD-ROMs, optical data storage devices, and/or any other suitable arrangements.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of recommending at least one patient interface device from among a plurality of patient interface devices as being suited to provide treatment in the form of respiratory therapy to a patient, the method comprising:

individually presenting each patient interface device, or a representation of each patient interface device, of the plurality of patient interface devices to the patient one at a time;

monitoring one or more characteristics of the patient indicative of a stress response of the patient while each patient interface device or representation thereof of the plurality of patient interface devices is presented to the patient;

determining from the monitoring a stress response of the patient corresponding to each patient interface device or representation thereof of the plurality of patient interface devices;

identifying the at least one patient interface device from among the plurality of patient interface devices that has a corresponding stress response less than one or more other patient interface devices of the plurality of patient interface devices; and providing the identified patient interface device to the patient.

2. The method of claim 1, wherein individually presenting each patient interface device, or a representation of each patient interface device, of the plurality of patient interface devices to the patient one at a time comprises providing an actual sample of each patient interface device to the patient.

3. The method of claim 1, wherein individually presenting each patient interface device, or a representation of each patient interface device, of the plurality of patient interface devices to the patient one at a time comprises providing an image of each patient interface device to the patient.

4. The method of claim 3, wherein providing a number of images of each patient interface device to the patient comprises providing a digital image of each patient interface device to the patient via a display.

5. The method of claim 1, wherein monitoring one or more characteristics of the patient indicative of a stress response of the patient while each patient interface device or representation thereof of the plurality of patient interface devices is presented to the patient comprises monitoring one or more of: heart rate variability (HRV), blood pressure, the breathing pattern, the galvanic skin response (GSR), brain waves (EEG), limb/head/body movements, or facial expressions.

6. The method of claim 5, wherein monitoring one or more characteristics of the patient indicative of a stress response of the patient while each patient interface device or representation thereof of the plurality of patient interface devices is presented to the patient is carried out using one or more of: an optical sensor, an accelerometer, a bioimpedance sensor, a flow sensor, a $CO_2$ sensor.

7. The method of claim 5, wherein:

individually presenting each patient interface device, or a representation of each patient interface device, of the plurality of patient interface devices to the patient one at a time comprises individually presenting physical samples of each patient interface of the plurality of patient interface devices to the patient; and monitoring the one or more characteristics of the patient indicative of a stress response of the patient comprises using one or more sensors integrated into each physical sample.

8. The method of claim 1, wherein outputting a recommendation to provide treatment in the form of treating the patient with respiratory therapy using the at least one patient interface device from among the one or more patient interface devices comprises providing the at least one patient interface device to the patient.

* * * * *